United States Patent [19]

Steppe et al.

[11] Patent Number: 4,983,160
[45] Date of Patent: Jan. 8, 1991

[54] RIGID TRANSPARENT FLUID CONDUIT FOR OPHTHALMIC SURGICAL IRRIGATION

[75] Inventors: Dennis L. Steppe, Anaheim; Stephen W. Haines, Tustin, both of Calif.

[73] Assignee: Nestle S.A., Fort Worth, Tex.

[21] Appl. No.: 276,550

[22] Filed: Nov. 28, 1988

Related U.S. Application Data

[63] Continuation-in-part of Ser. No. 119,268, Nov. 9, 1987, Pat. No. 4,787,889, which is a continuation of Ser. No. 780,813, Sep. 27, 1985, abandoned.

[51] Int. Cl.$^5$ ............................................. A61B 17/20
[52] U.S. Cl. ........................................ 604/22; 604/27; 604/35
[58] Field of Search ............................. 604/22, 27–35, 604/43, 264; 128/305

[56] References Cited

U.S. PATENT DOCUMENTS

| 4,787,889 | 11/1988 | Steppe et al. | 604/27 |
| 4,816,017 | 3/1989 | Hood et al. | 604/22 |
| 4,897,079 | 1/1990 | Zalecki et al. | 604/22 |

Primary Examiner—John D. Yasko
Assistant Examiner—Anthony Gutowski
Attorney, Agent, or Firm—Vorys, Sater, Seymour & Pease

[57] ABSTRACT

An improved irrigation fluid conduit for use with a coaxial surgical irrigator-aspirator for ophthalmic surgery. The conduit includes a hollow body adapted for attachment to the surgical irrigator-aspirator and a thin-walled tubular sleeve extending from the hollow body to surround the aspiration conduit of the instrument. The body and sleeve are homogeneously molded from polypropylene, which permits a rigid thin wall sleeve having a wall thickness not greater than 0.006 inches and a length-to-wall thickness ratio of more than two, and which is transparent when immersed in the aqueous humor of the eye for increased visibility by the surgeon of the adjacent tissues.

43 Claims, 2 Drawing Sheets

4,983,160

RIGID TRANSPARENT FLUID CONDUIT FOR OPHTHALMIC SURGICAL IRRIGATION

This is a continuation-in-part of copending application Ser. No. 119,268 filed on Nov. 9, 1987 which is a continuation of Ser. No. 780,813 filed Sept. 27, 1985 now abandoned and whose entire contents are hereby incorporated by reference.

BACKGROUND OF THE INVENTION

In performing delicate surgical procedures within the anterior chamber of the eye, it is necessary to make at least one penetrating incision passing through the peripheral tissues of the eye such as the cornea, the sclera, and the like. A particularly common procedure is the removal of a cataract by ultrasonic fragmentation and aspiration through a small-diameter ultrasonically-vibrated needle having an axial aspiration conduit, which is inserted through an incision just large enough to accomodate the diameter of the tool. Fluid leakage though the incision as well as removal of aqueous humor by aspiration through the ultrasonic needle lead to loss of the aqueous humor from the interior of the eye. If this fluid is not replaced, the anterior chamber of the eye will collapse, with serious consequences for the health of the eye, particularly for the delicate corneal endothelium. Accordingly, in order to prevent this collapse a supply of irrigating fluid is provided to the interior of the eye, either through a secondary incision in the eye or by means adapted for both irrigation and aspiration through a single incision. The single incision method is generally preferred, but it requires an irrigation-aspiration apparatus having a double lumen tube with the separate channels for irrigation and aspiration placed either side by side or coaxially. The coaxial configuration has certain advantages, especially for ultrasonic surgical instruments having provision for irrigation and aspiration. Such an instrument which incorporates an ultrasonic fragmenting and aspirating needle and a coaxial irrigation conduit is disclosed, for example in Banko and Kelman, U.S. Pat. No. 3,589,363, whose entire contents are hereby incorporated by reference.

The performance requirements of a sleeve which defines the irrigating channel in a coaxial surgical irrigator/aspirator place severe demands on the materials and design of the sleeve. The sleeve should have a low heat conductivity to insulate the tissue at the sides of the incision from heat generated by friction with the ultrasonic tool. It should be sufficiently strong to prevent collapse under pressure from the sides of the incision. At the same time it should have the smallest diameter possible to allow a minimum size incision. It is also helpful if the sleeve is transparent to provide better visibility for the surgeon. Finally, because the element is small and of rather precise dimensions, it is desirable that it be capable of being formed by molding for economical manufacture thereof.

Each of the materials previously used in the fabrication of such irrigation sleeves has had certain drawbacks. Metal sleeves, such as stainless steel, have the advantage of rigidity, which makes them easier to insert through a small incision and less likely to injure the ocular tissues such as the corneal endothelial cell layer and Descemet's membrane. Since they cannot be collapsed by pressure from the sides of the incision, they make it easier to assure a constant flow rate of irrigation fluid. However, because of their extreme rigidity, they must be very precisely matched to the shape of the interior aspiration conduit, so that many different sleeves are needed to accomodate various aspiration conduits. Furthermore, because of their heat conductivity, they do not protect the adjacent tissues from heat generated when the aspiration conduit is an ultrasonically vibrated surgical tool. Accordingly, metal sleeves have hitherto not been used with ultrasonic surgical instruments but only with simple irrigation-aspiration devices.

Synthetic resins, in the cross-sections required for irrigation sleeves, tend to be lacking in rigidity and/or strength. This requires a larger incision, either to accommodate a larger wall thickness or to minimize the forces from the sides of the incision which tend to collapse the sleeve. Furthermore, some plastics are not transparent, and, like metal sleeves, obscure the surgeon's vision. U. S. Pat. No. 3,589,363 (which is hereby incorporated in its entirety) recommends the use of a sleeve of polytetrafluoroethylene, which is inert, but difficult to fabricate and is not perfectly transparent, even in thin sections. A commonly used commercial irrigation sleeve is made from silicone rubber and is molded integrally with a cap for fastening the sleeve to the ultrasonic handpiece. Silicone rubber can be conveniently molded by injection molding, but it is flexible and tends to collapse under pressure from the incision and to fold back on itself or "telescope" when inserted through the incision. Furthermore, it is at best translucent, so that the surgeon's vision is somewhat obscured.

Hence a need has continued to exist for a surgical irrigation conduit which is free from the drawbacks of the known irrigation conduits.

SUMMARY AND OBJECTS OF THE INVENTION

It has now been found that an irrigation conduit having a sufficiently rigid wall with a wall thickness sufficiently small to be used as a sleeve in a coaxial surgical irrigation-aspiration instrument and thereby to allow a conveniently small incision can be molded from certain polyolefin synthetic resins, particularly from polypropylene.

Accordingly, it is an object of this invention to provide a rigid irrigation or infusion sleeve which is easily inserted into a small incision.

Another object is to to provide a rigid infusion sleeve which can be used with irrigation/aspiration handpieces with or without ultrasonic fragmentation.

A further object is to provide a rigid infusion sleeve which makes it easier to maintain fluidic balance through a small incision.

A still further object is to provide a generally transparent infusion sleeve which improves the visibility of the irrigation/aspiration or ultrasonic fragmenting tip and of the ocular structures during use.

Another object is to provide a rigid infusion sleeve which reduces the incidence of trauma to ocular tissues when inserted therein.

A further object is to provide a rigid, transparent fluid conduit for ophthalmic surgical irrigation to nullify or discourage attempts to reclean and sterilize it.

A still further object is to provide a low cost ophthalmic fluid conduit design which discourages attempts for expensive and/or incomplete recleaning and autoclave resterilization procedures thereof.

Another object is to provide an improved ophthalmic conduit sleeve having a smoothness allowing for easy insertion into the eye and a rigidity sufficient for sustained fluid flow therethrough when in tight wounds.

A further object is to provide an improved conduit sleeve design which minimizes wound leakage due to tighter wounds and reduces the chance of anterior chamber shallowing during surgery.

A still further object is to provide an improved, ophthalmic surgical irrigation fluid conduit whose low cost and mass manufacture make it truly disposable.

Other objects and advantages of the present invention will become apparent to those persons having ordinary skill in the art to which the present invention pertains from the foregoing description taken in conjunction with the accompanying drawings.

DETAILED DESCRIPTION OF THE PREFERRED EMBODIMENTS

Figure 1:
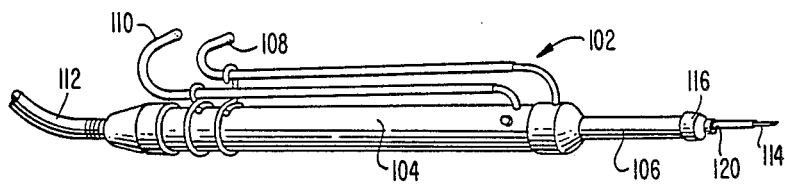
FIG. 1 shows an ultrasonic surgical irrigator-aspirator of the type which incorporates a tip cap/sleeve member which acts as an irrigation conduit.

The rigid infusion sleeve of this invention is designed to function as a part of a conventional ophthalmological surgical tool which incorporates coaxial irrigation and aspiration functions. An illustrative surgical instrument of this type wherein an elongated surgical tool or needle is ultrasonically vibrated to fragment tissue is depicted in FIG. 1. While the illustrated surgical instrument is capable of ultrasonic tissue fragmentation, the invention is equally applicable to surgical instruments designed only for irrigation and aspiration. The surgical tool of this ultarsonic type comprises a handpiece shown generally at 102 having a barrel 104 and an extension 106 which suppports an ultrasonically-vibrated surgical tool or needle 114. The handpiece is provided with a cable 112 containing power and control wires and cooling water tubes. The instrument is also provided with an aspiration line 110 which is connected to a source of vacuum and an irrigation line 108 connected to a source of irrigation fluid. Both lines ar connected to passages within the handpiece leading to the region of the tip of the handpiece. The distal end of the handpiece is provided with an adapter 116 and a tip cap and sleeve member 120 which surrounds the ultrasonic tool 114 and provides a coaxial annular passage for supplying irrigation fluid to the surgical site.

Figure 2:
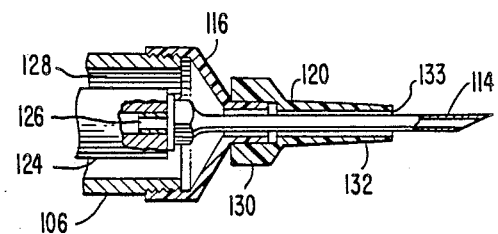
FIG. 2 shows a longitudinal section of the tip portion of the irrigator-aspirator of Figure showing the attachment of the tip cap and sleeve member to the handpiece.

FIG. 2 shows a detailed cross-section of the distal end of the handpiece 102. The ultrasonic needle 114 is fastened to the ultrasonically-vibrating connecting member 124 by a threaded connection. An axial bore 126 in the ultrasonic tool communicates through conventional drilled passages in the ultrasonic connecting member 124 and the handpiece (not shown) with the aspiration line 110. The region between the ultrasonic connecting member 124 and the extension 106 provides a conduit 128 for irrigation fluid. This conduit is connected by conventional channels (not shown) in the handpiece 102 to the irrigation fluid line 108. The tip cap and sleeve member 120 fits on the end of the adapter 116, and is made up of a body member 130 and a sleeve member 132. The body member and sleeve member are preferably molded homogeneously from one synthetic resin material. The tip cap and sleeve member 120 surrounds the ultrasonic tool 114 to provide a coaxial fluid channel 133 which receives fluid from the fluid channel 128 and conducts it to the surgical site.

The tip cap/sleeve 132 of this invention has a body portion 130 which is hollow and has means for engaging the front end of the surgical instrument so as to be in fluid communication with the passage or passages in the handpiece which supply irrigation fluid. The body portion of the tip cap and sleeve surrounds the ultrasonically-vibrated needle and has an axis which is coincident with the axis of the ultrasonically-vibrated needle. Generally, the body portion is cylindrical in shape and has a relatively thick wall provided with fastening means at one end of the body for engaging the end of the handpiece to be retained thereon. In the embodiment illustrated in FIG. 2, the means for engaging the end of the handpiece is simply the internal bore of the body member 130 which is press fit for the end of the adapter 116. Preferably, the fastening means are internal threads 140 on the wall of the body portion 130 (as shown in FIG. 4) which threadably engage external threads on the end of the handpiece to fasten the tip cap and sleeve thereto.

The sleeve portion of the tip cap and sleeve of the invention is molded homogeneously with the body portion and is a tubular member having an axis coaxial with the axis of the body member and a wall thickness not greater than 0.006 inches. The cap and sleeve should be molded of a synthetic resin material which provides sufficient rigidity to prevent collapse under the pressure of the sides of the ocular incision, with accompanying decrease in irrigation and danger of excessive heating of the adjacent tissue. The synthetic resin used in the tip cap and sleeve should also be transparent so as not to obscure the surgeon's view of ocular structures, and preferably has a refractive index close to that of water, so that it becomes practically invisible when immersed in the aqueous humor of the eye, particularly the human eye; this properly enhances the surgeon's view of the surgical site, and the tool. Polyolefin resins having sufficient rigidity to resist collapse are suitable materials for forming the fluid conduit of this invention. Such materials are obtainable in grades which are substantially transparent in thin wall sections and have a refractive index close to that of the aqueous humor and the irrigation fluid whereby they are substantially invisible in use and do not obstruct the surgeon's vision. Conventional polypropylene molding philosophy prior to this invention apparently had thought that with the required rigidity and desired transparency as described herein it was not possible to mold the conduit sleeve due to the thin (0.006 inch or less) wall thickness required.

Figure 3:
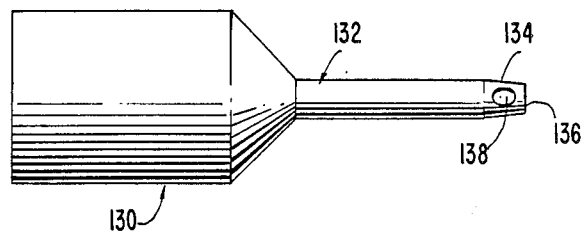
FIG. 3 shows a side elevation of a tip cap and sleeve member of this invention.

A preferred embodiment of the fluid conduit of this invention is shown in FIG. 3. The body member 130 and sleeve member 132 are molded homogeneously of one synthetic resin material. The radiused annulus distal tip 136 of the fluid conduit is sized to fit closely over the aspiration member of a surgical irrigator-aspirator and is provided with a tapered section 134 for easy insertion into the incision. Since infusion holes 138 are also formed in the sleeve member 132 to provide free flow of irrigation fluid to the surgical site.

Figure 4:
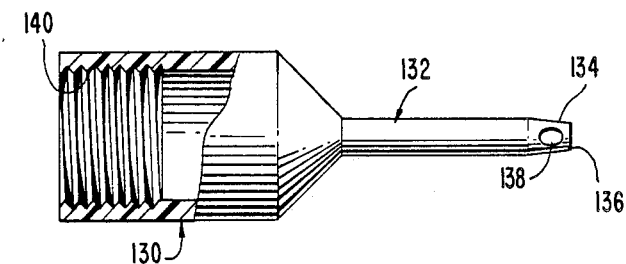
FIG. 4. shows a partial longitudinal section of a molded tip cap/sleeve of this invention.

FIG. 4 shows a partial section of the embodiment of FIG. 3 showing the internal threads 140 in the wall of the body member 130 which provide means for attaching the fluid conduit of the invention to the surgical irrigator-aspirator.

Figure 5:
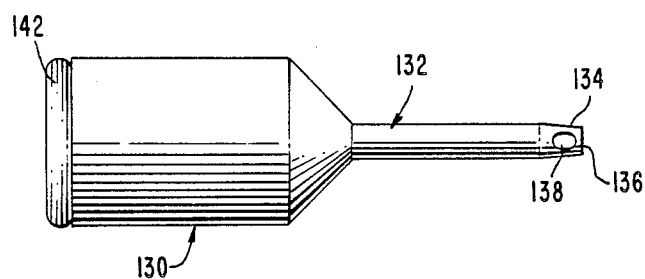
FIG. 5 shows a preferred embodiment of the fluid conduit of the invention incorporating an overmolded sealing ring.

FIG. 5 shows a preferred embodiment of the fluid conduit of the invention having a sealing ring 142 attached to the end of the body member 130. Preferably the sealing ring is made of a synthetic resin material selected for its sealing ability and is overmolded to form an integral part of the body member 130. A preferred material for the sealing ring is an elastomer, such as polyvinyl chloride. The present invention contemplates a sealing ring which is incompatible with autoclave sterilization.

The junction of the polypropylene body with the overmolded polyvinyl chloride o'ring is in direct contact with the irrigation fluid path internally to the body. Hence, it defines a potential bacterial trap which must be dealt with during any proposed recleaning and resterilization procedure and thereby produces a formidable barrier to any contemplated reuse, and health hazards to the patient exist if reuse is attempted. Thus the construction of the present conduit discourages such action. Further since the present device is designed for the low cost, mass manufacture, the expense of recleaning and resterilization is discouraged.

A preferred material for the tip cap and sleeve of this invention is polypropylene. This material has the capability of being molded by injection molding in the thin wall sections which are required in the tip cap sleeve of this invention. It also has sufficient rigidity to prevent collapse of the sleeve under the normal compressive stress induced by contact with the sides of the incision. The material is also transparent and has a refractive index relatively close to that of the aqueous humor of the eye, so that, in use the sleeve is substantially invisible, and does not obstruct the surgeon's view. The sleeve portion has a light transmissivity, preferably at least 68%. This represents about twice as much light passing through it than that of the blue silicone tip cap/sleeve currently available. Although a clear silicone sleeve would allow more light to pass through it, it would be unacceptable as subject to the undesirable and critical telescoping and crimping effects discussed above and which are not experienced by the subject rigid sleeve. The tubular sleeve portion has a length-to-wall thickness ratio of more than two and in certain instances the ratio is more than 65 and in other circumstances is at least 75. Moreover, the sleeve portion is made of a material which results in unacceptable material deterioration thereto following standard gamma sterilization thereof.

The tip cap and sleeve of this invention is preferably made from polypropylene having a melt flow rate by ASTM D1238 of 9.0–12.0 grams/10 minutes, preferably 10.0–11.0 grams/10 min. The polypropylene preferably has a weight-average molecular weight, as measured by gel permeation chromatography, of about 220,000 to about 280,000, and more preferably about 250,000. This polypropylene material also minimizes heat transfer to the cornea by the ultrasonic cutting tip.

Unlike the polyolefin synthetic resin sleeve of the present invention, the prior art metal, polytetrafluoroethylene, synthetic resins, and silicone rubber irrigation sleeves are not adequately transparent when immersed in the aqueous humor of the eye and thus do not provide for improved visualization of the ultrasonic cutting tip and structure to assist the surgeon in delicate ophthalmological surgery and surgical irrigation. When immersed in the aqueous humor, only a faintly discernible outline of the subject sleeve is visible thereby allowing full visualization of the ultrasonic cutting tip and the adjacent tissues at all times by the surgeon. Furthermore, cavitation bubbles appear to be reduced by the present design, thereby further increasing visualization and reducing undesirable effects of cavitation.

The present invention further affords freedom from wound-induced pinching-off of the very thin wall sleeve section as experienced with the prior art devices. This s due to the sleeve sections ability to resist collapse, i.e., diametric rigidity, from wound pressure as compared to less rigid sleeves made of elastometric materials, such as silicone rubber. The sections have a diametric rigidity requiring a force of at least 0.8 pounds for a 10% compression and 2.0 pounds for a 50% compression. Furthermore, the lubricity of the object device allows for easy insertion into the eye with consequent minimal cellular damage plus a low coefficient of friction and minimal sleeve shedding against an energized ultrasonic cutting tip should there be inadvertent contact between the sleeve and cutting tip.

Further due to the construction and particular selected material this rigid, transparent fluid conduit for ophthalmic surgical irrigation is effectively unable to be recleaned and resterilized and thereby is limited to a single use. This limitation though accords with the prevailing thought and philosophy of the ophthalmic medical community favoring disposable, single use medical devices (ref: Accreditation Manual for Hospitals, 1982).

The molding procedure for manufacturing the tip cap and sleeve of the invention is generally conventional but requires the usual care needed for molding thin sections in polypropylene. The mold is designed to be vented at the distal end of the irrigation sleeve core pin by means of a small vent machined into the mold to allow complete filling of the mold during injection of the molten resin. Preferably the mold is designed to provide for molding the ports at the distal end of the sleeve to eliminate a punching operation on the finished product. The completed molded unit is preferably flame treated on the distal end of the sleeve to remove any molding flash. The tip cap and sleeve of the invention may be molded in an injection molding machine of either the toggle clamp or hydraulic clamp type. In either case the mold-fill injection time should be about 8.0 seconds at a pressure of about 7000 psi. The injection time is somewhat critical in order to prevent material shearing and consequent burning of the material during mold-fill. After the injection phase, a part cooling cycle of about 11.0 seconds takes place, and the mold is then opened and the finished part is ejected. The nozzle temperature of the injection molding machine should be about 520°±20° F. for a toggle-clamp molding machine and about 500°±0° F. for a hydraulic clamp machine. In each case the clamp setting or clamp pressure should be backed off before the mold is filled to provide about 0.0008 inch parting line venting to assure complete filling of the mold during the material fill cycle.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. For use with an ophthalmological surgical instrument providing irrigating and aspirating functions, having an elongated handpiece containing an irrigation fluid supply conduit, and having an elongated tool connected to the handpiece, an irrigation fluid conduit comprising:

a hollow body portion including body walls surrounding an axis, a first end open for fluid transmissive communication with the irrigation fluid supply conduit, a second end having an axial opening therein, and an engaging means for engaging said handpiece;

a tubular sleeve portion in fluid transmissive communication with said axial opening in said second end and coaxially extending therefrom, configured to surround the too, and having a thin sleeve wall whose thickness is not greater than 0.006 inches;

said hollow body portion and said tubular sleeve portion being homogeneously molded from a polyolefin synthetic resin which is transparent when immersed in the aqueous humor of the eye, so that, when said engaging means engages the handpiece, the tool, when in the eye, and the adjacent tissues can be visualized by the surgeon through said sleeve portion, and which has a diametric rigidity great enough to prevent collapse of said sleeve when it is inserted into an ocular incision;

an elastomeric sealing ring overmolding said first end opening of said body section; and, said tubular portion has a sleeve length-to-wall thickness of more than two.

2. The conduit of claim 1 including, said polyolefin synthetic resin being polypropylene.

3. The conduit of claim 2 including said polypropylene having a melt flow index by ASTM D1238 of 9.0–12.0 grams/10 minutes.

4. The conduit of claim 3 including said melt flow index being 10.0–11.0 grams/10 minutes.

5. The conduit of claim 2 including, said polypropylene having a molecular weight of about 220,000 to about 280,000.

6. The conduit of claim 5 including, said molecular weight being about 250,000.

7. The conduit of claim 3 including, said polypropylene having a melt flow index by ASTM D1238 of 10.0 to 11.0 grams/10 minutes and a molecular weight of about 250,000.

8. The conduit of claim 1 including, said wall thickness being not less than 0.005 inch.

9. The conduit of claim 1 including, said wall thickness being 0.0055 inch.

10. The conduit of claim 1 including, said engaging means including internal threads generally adjacent said open end of said body portion.

11. The conduit of claim 1 including, said body portion being generally cylindrical.

12. The conduit of claim 1 including, said sleeve portion having a light transmissivity of at least 68%.

13. The conduit of claim 1 including, said length-to-thickness ratio being more than 65.

14. The conduit of claim 13 including, said length-to-thickness ratio being at least 75.

15. The conduit of claim 1 including, said sleeve portion resulting in unacceptable material deterioration thereto following standard gamma sterilization thereof.

16. The conduit of claim 1 including, said resin being easy flowing to fully fill said thin sleeve wall.

17. The conduit of claim 1 including, said sealing ring being formed of a material which is incompatible with autoclave sterilization.

18. The conduit of claim 17 including, said material of said sealing ring being polyvinyl chloride.

19. An ophthalmological surgical instrument providing irrigating and aspirating functions comprising:

(A) an elongated handpiece;

(B) an irrigation fluid supply conduit positioned in said handpiece;

(C) an elongated tool connected to said handpiece; and (D) an irrigation fluid conduit comprising:

a hollow body portion including body walls surrounding an axis, a first end open for fluid transmissive communication with said irrigation fluid supply conduit, a second end having an axial opening therein, and an engaging means for engaging said handpiece, a tubular sleeve portion in fluid transmissive communication with said axial opening in said second end and coaxially extending therefrom, configured to surround said too, and having a thin sleeve wall whose thickness is not greater than 0.006 inch, said hollow body portion and said tubular sleeve portion being homogeneously molded from a polyolefin synthetic resin which is transparent when immersed in the aqueous humor of the eye, so that said too, when in the eye, and the adjacent tissues can be visualized by the surgeon through said sleeve portion, said sleeve portion having a light transmissivity of at least 68%, and which has a diametric rigidity great enough to prevent collapse of said sleeve portion when inserted into an ocular incision, an elastomeric sealing ring overmolding said first end opening of said body section, and, said sleeve portion resulting in unacceptable material deterioration thereto following standard gamma sterilization thereof.

20. The instrument of claim 20 including, said tool comprising a surgical aspiration tool.

21. The instrument of claim 20 including, said surgical aspiration tool being an ultrasonically-vibrated surgical aspiration tool.

22. The instrument of claim 19 including, said tool including an ultrasonically-vibrated surgical needle.

23. The instrument of claim 19 including, said tool having a tip, and said sleeve portion having the distal end thereof having an internal radius large enough to provide for transition therethrough of said tip of said tool.

24. The instrument of claim 19 including, said handpiece being generally cylindrical.

25. The instrument of claim 19 including, an elongated tubular aspiration fluid supply conduit at one end of said handpiece.

26. The instrument of claim 19 including, said polyolefin synthetic resin being polypropylene.

27. The instrument of claim 26 including,
said polypropylene having a melt flow index by ASTM D1238 of 9.0–12.0 grams/10 minutes.

28. The instrument of claim 27 including,
said melt flow index being 10.0–11.0 grams/10 minutes.

29. The instrument of claim 26 including,
said polypropylene having a molecular weight of about 220,000 to about 280,000.

30. The instrument of claim 29 including,
said molecular weight being about 250,000.

31. The instrument of claim 26 including,
said polypropylene, having a melt flow index by ASTM D1238 of 10.0 to 11.0 grams/10 minutes and a molecular weight of about 250,000.

32. The instrument of claim 19 including,
said wall thickness being not greater than 0.005 inch.

33. The instrument of claim 19 including,
said engaging means including internal threads generally adjacent said open end of said body portion.

34. The instrument of claim 19 including,
said body portion being generally cylindrical.

35. The instrument of claim 34 including,
said wall thickness being 0.0055 inch.

36. The instrument of claim 34 including,
said wall thickness being not less than 0.005 inch.

37. The instrument of claim 34 including,
said resin being easy flowing to fully fill said thin sleeve wall.

38. The instrument of claim 34 including,
said tubular sleeve portion having a length-to-thickness ratio of more than two.

39. The instrument of claim 38 including,
said length-to-thickness ratio being more than 65.

40. The instrument of claim 39 including,
said length-to-thickness ratio being at least 75.

41. The instrument of claim 19 including,
said sealing ring being formed of a material which is incompatible with autoclave sterilization.

42. The instrument of claim 41 including,
said material of said sealing ring being polyvinyl chloride.

43. For use with an ophthalmological surgical instrument providing irrigating and aspirating functions, having an elongated handpiece containing an irrigation fluid supply conduit, and having an ultrasonically-vibrated surgical needle connected to the handpiece, an irrigation fluid conduit comprising:

a hollow body portion including body walls surrounding an axis, a first end open for fluid transmissive communication with the irrigation fluid supply conduit, a second end having an axial opening therein, and an engaging means for engaging the handpiece, a tubular sleeve portion in fluid transmissive communication with said axial opening in said second end and coaxially extending therefrom, configured to surround the needle, and having a thin sleeve wall whose thickness is not greater than 0.006 inch, said hollow body portion and said tubular sleeve portion being homogeneously molded from a polyolefin synthetic resin which is transparent when immersed in the aqueous humor of the eye, so that, when said engaging means engages the handpiece, the needle, when in the eye, and the adjacent tissues can be visualized by the surgeon through said sleeve portion, and which has a diametric rigidity great enough to prevent collapse of said sleeve portion when it is inserted into an ocular incision, and said polyolefin synthetic resin being polypropylene having a melt flow index by ASTM D1238 of 9.00 to 12.0 grams/10 minutes and a molecular weight of about 220,000 to 280,000, and an elastomeric sealing ring overmolding said first end opening of said body section.

* * * * *